(12) United States Patent
Hardman et al.

(10) Patent No.: US 7,303,923 B2
(45) Date of Patent: Dec. 4, 2007

(54) BIOCHEMICAL AND IMMUNOCHEMICAL ASSAY DEVICE

(75) Inventors: David John Hardman, Herne Bay (GB); James Howard Slater, Cardiff (GB); Adam G. Reid, Whitstable (GB); William Kenneth Lang, Canterbury (GB); James Richard Jackson, Cliddesden (GB)

(73) Assignee: Diamatrix Limited, Hampshire (GB)

( * ) Notice: Subject to any disclaimer, the term of this patent is extended or adjusted under 35 U.S.C. 154(b) by 670 days.

(21) Appl. No.: 10/237,987

(22) Filed: Sep. 10, 2002

(65) Prior Publication Data
US 2003/0103869 A1    Jun. 5, 2003

Related U.S. Application Data

(63) Continuation of application No. 09/341,551, filed on Nov. 14, 1999, now Pat. No. 6,573,108, which is a continuation of application No. PCT/GB98/00136, filed on Jan. 15, 1998.

(30) Foreign Application Priority Data
Jan. 15, 1997   (GB)   ................................. 9700759.5

(51) Int. Cl.
  *G01N 33/543*   (2006.01)

(52) U.S. Cl. ....................... 436/518; 427/448; 427/466; 427/485; 427/491; 427/504; 427/505; 427/510; 436/514; 436/823; 435/970; 435/287.1; 435/7.1

(58) Field of Classification Search ............... 427/448, 427/466, 485, 491, 504, 505, 510; 436/518
See application file for complete search history.

(56) References Cited

U.S. PATENT DOCUMENTS 4,322,450 A  *  3/1982  Gray et al. ................. 427/504
5,409,664 A     4/1995  Allen
5,843,789 A  * 12/1998  Nomura et al. ............. 436/164

FOREIGN PATENT DOCUMENTS

| EP | 0690306 | 1/1996 |
| WO | WO 93/10457 | 5/1993 |
| WO | WO 93/24231 | 12/1993 |
| WO | WO 94/20215 | 9/1994 |

* cited by examiner

*Primary Examiner*—Bao-Thuy L. Nguyen
(74) *Attorney, Agent, or Firm*—Nixon & Vanderhye P.C.

(57) ABSTRACT

We describe an assay device which comprises (a) a substrate comprising: (i) a porous material capable of chromatographically transporting a liquid and (ii) one or more test reagents for an assay provided on the porous material; and (b) a water-impermeable coating polymer attached to the porous material so as to define a continuous bibulous compartment.

11 Claims, 6 Drawing Sheets

Fig.1.
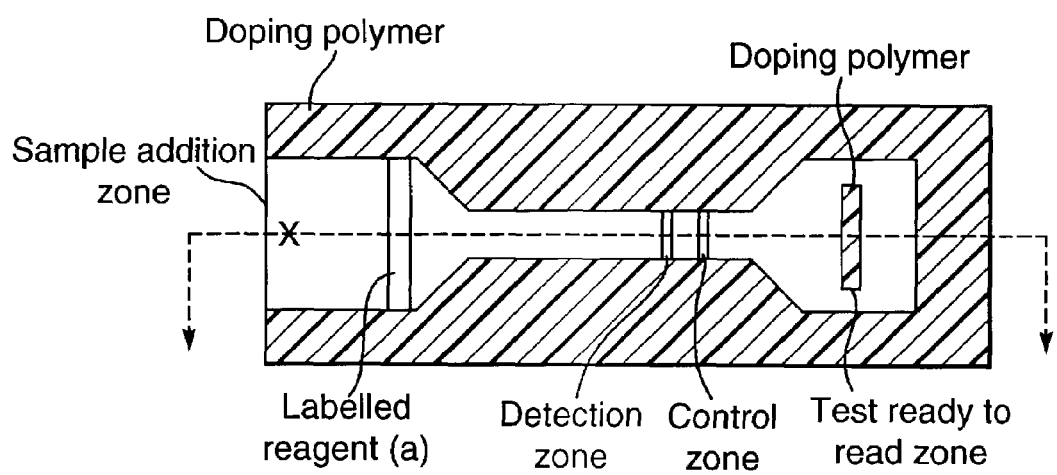
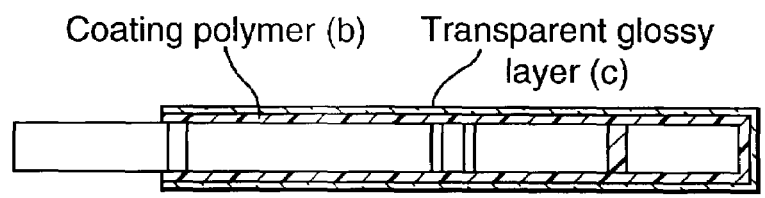

BIOCHEMICAL AND IMMUNOCHEMICAL ASSAY DEVICE

This application is a continuation of application Ser. No. 09/341,551, filed Nov. 14, 1999 now U.S. Pat. No. 6,573,108, allowed; which is a continuation under 35 U.S.C. §371 of PCT/GB98/00136, filed Jan. 15, 1998, the entire content of which is hereby incorporated by reference.

FIELD OF THE INVENTION

The present invention relates to a new device for conducting assays.

There is a continuing need for simple self-contained devices for performing biochemical assays outside the laboratory. In particular, there is a need for a device which can be used in the home, clinic or doctor's surgery, which can be used to give an analytical result which is rapid and which requires the minimum degree of skill and involvement from the user.

BRIEF DESCRIPTION OF THE DRAWINGS

FIG. 1 illustrates an assay device in which the test reagents are provided on the porous material.

Figure 2:
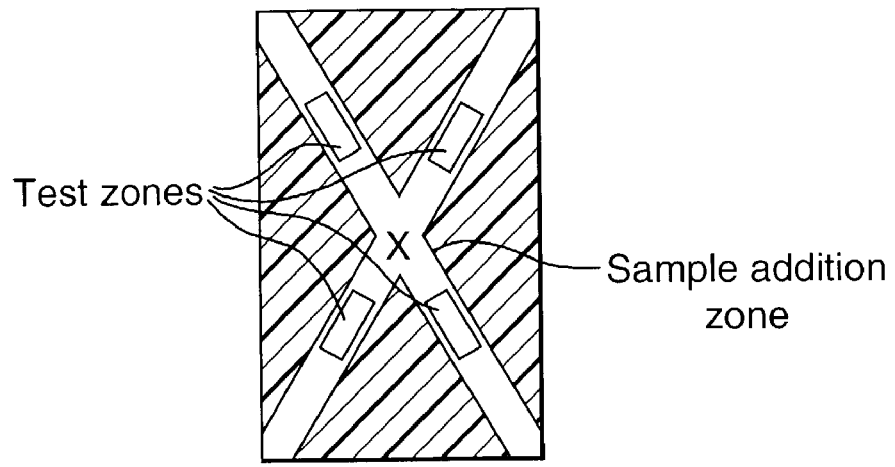
FIGS. 2 and 3 illustrate a bibulous compartment having a central body with a plurality of channels connected thereto.

The present invention seeks to provide a device for conducting biochemical assays, which avoids the need for complicated manual procedures and which therefore can be operated by an unqualified user.

Accordingly, the present invention provides an assay device comprising:
(a) a substrate comprising:
  (i) a porous material capable of chromatographically transporting a liquid; and
  (ii) one or more test reagents for an assay provided on the porous material; and
(b) a transparent water-impermeable coating polymer attached to the porous material so as to define a continuous bibulous compartment.

Typically, the porous material is a cellulosic material, a porous plastics material or a glass fibre material. Preferably, the porous material is a cellulosic material such as paper or nitrocellulose. The porous material may be chemically or physically modified to provide for specific physiochemical properties. For example it may carry an ionic charge, particularly when it is paper. Examples of suitable charged porous material include Whatman® ion exchange paper.

Preferably, a doping polymer impermeable to the liquid which the porous material is capable of transporting is incorporated into a part of the porous material so as to define a channel in the porous material, the or each test reagent being provided on the porous material in the channel defined therein. Typically, the doping polymer is an acrylic polymer, an acrylic copolymer such as a copolymer of ethylacrylate and methyl methacrylate such as Primal B-60A, a vinyl acrylic copolymer such as a screen printing ink such as Polyvin Gloss or a heteropolysaccharide. Suitable heteropolysaccharides include carrageenan polymers such as Type II carrageenan. A silane may be used together with the doping polymer to delimit the channel in the porous material.

The shape of the bibulous compartment can be determined by the shape of the porous material, but is preferably determined by the channel defined in the porous material by the doping polymer.

The polymer (b) coats the substrate. It is typically bonded to the substrate (a) and cannot be mechanically removed. Preferably, the coating polymer (b) is bonded to the substrate by partial penetration of the coating polymer into the substrate. Thus, the coating polymer (b) is preferably contiguous with, or integral to, the assay device. The coating polymer penetrates the substrate only to a limited extent and does not penetrate to such an extent so as to prevent the porous material from chromatographically transporting the liquid. Generally, the coating polymer penetrates from 30 to 70%, preferably about 50%, of the thickness of the substrate.

The coating polymer (b) is typically a heteropolysaccharide and is preferably a carrageenan polymer such as Type I carrageenan or agarose. It may also be a synthetic polymer such as an acrylic polymer or an acrylic copolymer such as Primal B-60.

The coating polymer (b) need not coat the entire substrate (a). A part of the porous material may thus be uncoated. Preferably, however, there is only one entrance to the bibulous compartment. One or more (but not all) of the test reagents may be provided on the uncoated portion of the porous material in such a way as to be chromatographically transported into the bibulous compartment when a liquid sample is applied to the assay device. Thus, the coating (b) typically coats at least a part of the porous material so as to define a continuous bibulous compartment containing at least one test reagent.

Preferably, the assay device of the present invention comprises a further layer (c) provided on the coating polymer (b) to improve the visual and/or textural properties of the assay device. The layer (c) may be transparent, glossy, rigid or water-impermeable as required. Preferably, it is a transparent glossy layer. The layer (c) may advantageously also be printable, that is, able to have information printed directly onto it. Examples of information which can be printed onto the layer (c) include logos, brand names, instructions for using the assay device, indicators to show a positive and/or negative result, calibration standards and barcodes.

Typically, the layer (c) comprises one or more compound(s) selected from acrylic polymers such as polymethacrylic acid, acrylic copolymers such as Acrylsol WS-24, Primal B-85 and copolymers of ethylacrylate and methyl methacrylate (for example Primal B-60A), polyuronic acids such as alginic acid, and polymeric alcohols. Preferred polymeric alcohols are those having a molecular weight of from 6000 to 146000, preferably about 9000. Suitable polymeric alcohols include polyvinyl alcohol.

Where the polymer (b) does not coat the entire substrate (a), the layer (c) typically does not coat that part of the porous material which is not coated with the polymer (b).

The assay devices of the invention can be used in assaying a wide range of liquid samples for a wide range of analytes. Thus, they can be used in human or animal healthcare, for example to assay samples such as human or animal serum, plasma, urine, saliva or cerebrospinal fluid for analytes such as blood glucose, drugs of abuse, therapeutic drugs, and antigens of diagnostic significance and antibodies therefor. They can also be used in food hygiene, for example to assay food products for pathogens such as *E. coli* or *Salmonella*, or to assay drinking water for pathogens such as those causing cholera, typhoid or amoebic diseases. Further, they can be used in environmental testing, for example to assay river water for pollutants such as phosphates, nitrates, nitrites or a range of xenobiotic compounds such as polyaromatic hydrocarbons, total petroleum hydrocarbons and polychlorinated biphenyls. As the devices are simple and self contained, they can be used in many situations. For example, they can be used for field application at polluted sites and in domestic environments, for example to assay water from an aquarium for nitrites or nitrates.

Generally speaking, the sample to be assayed will be an aqueous sample and the liquid which the porous material is capable of transporting is therefore generally an aqueous liquid.

The test reagents provided on the porous material of the assay device generally comprise at least one detection reagent that is capable of reacting with a predetermined analyte whose presence is suspected in a sample to be assayed to generate a detectable effect, for example by forming a complex with the predetermined analyte. The detectable effect may be apparent to the naked eye (e.g. a colour change). Alternatively, it may be detectable only by a spectrometer or other technical means (e.g. a change in ultraviolet absorption).

Typically, the detection reagent has a greater affinity for the predetermined analyte than for other ingredients of the sample to be assayed.

The detection reagent can be a chemical such as ferric ions, which undergo a colour change when contacted with salicylic acid, picric acid, which forms a coloured complex with creatinine under alkaline conditions, and ammonium molybdate, which forms a complex with phosphate ions under acidic conditions.

The detection reagent may also be an enzyme, for example alcohol dehydrogenase which, together with nicotinamide adenine dinucleotide, can convert ethanol to acetaldehyde, which conversion is detectable using ultraviolet light.

More than one detection reagent may be used, if required. Thus, an enzyme and a coenzyme may be used as detection reagents. Examples of cases where more than one detection reagent may be used include the use of sulphanilamide and napthylethylenediamine, which form a pink complex with nitrite ions under acid conditions, and the use of glucose oxidase, phenol, 4-aminoantipyrene and peroxidase to detect glucose. Where more than one detection reagent is present, each detection reagent may be provided on adjacent parts of the porous material, or one or more of the detection reagents may be provided on the same part of the porous material. Where more than one detection reagent is used, the detectable effect is in general produced only after each detection reagent is contacted with the liquid sample in whose presence the analyte is suspected.

Generally, at least one reagent is immobilised on the porous material. It may be immobilised by passive adsorption to the porous material. Alternatively, the test reagents may comprise a detection anchor compound which is capable of immobilising a detection reagent on the porous material. The detection anchor compound may be a compound allowing suitable covalent bonding between the porous material and the detection reagent.

The detection reagent may also be immobilised on the porous material by ionic means. For example, negatively charged ion exchange paper can be used as the porous material to immobilise a charged detection reagent (or vice versa). Examples of charged detection reagents include mixtures of sulphanilamide and N-1-naphthylethylenediamine dihydrochloride, which mixtures can be used to detect nitrite as discussed above.

The test reagents may comprise, in addition to the detection reagent, a reagent to enhance the detectable effect caused by the reaction of the predetermined analyte with the detection reagent. For example carboxy methyl cellulose may be present when the porous material is paper, to ensure distribution of a coloured reaction product across the paper.

The or each detection reagent can, for example, be arranged so as to give, as detectable effect, a band of colour or may be arranged to give, as detectable effect, a block of colour. The latter arrangement may be useful for quantitative or semi-quantitative assays involving a comparison of the intensity of the obtained colour with a standard.

The assay devices of the invention can be used to conduct multi-reagent chemical assays or sequential assays. Thus, a first detection reagent and at least one further detection reagent may be provided on the porous material, the relative positioning of the reagents being such that a liquid sample applied to the bibulous compartment will be chromatographically transported to first contact the first reagent and then to contact the further reagents.

Typically, in assay devices suitable for multi-reagent chemical assays, each detection reagent except the last detection reagent to be contacted by the liquid sample is freely mobile when a liquid is applied to the porous material, the said last detection reagent to be contacted being immobilised on the porous material in a manner as explained above. Typically, in assay devices suitable for sequential assays, each detection reagent is immobilised on the solid support in a manner explained above.

For example, when a multi-reagent assay device having two detection reagents is used, a liquid sample in whose presence the analyte is suspected will be chromatographically transported to the first reagent where the analyte, if present, will undergo a first reaction. The product of the first reaction will be chromatographically transported to the second (and last) detection reagent, which is typically immobilised on the porous material. There it will undergo a second reaction to generate a detectable effect. When the first reagent is sulphanilamide and the second reagent is naphthylethylenediamine, the assay device is suitable for assaying a liquid sample for the presence of nitrite.

As a further example, when a sequential assay device is used, each detection reagent is typically immobilised on the porous material and the liquid sample is chromatographically transported across each detection reagent. Each detection reagent may be capable of reacting with a different analyte to produce a detectable effect (in which case the sequential assay device will be suitable for assaying a liquid sample for a plurality of analytes). Alternatively, each detection reagent may be sensitive only to a predetermined concentration of an analyte (in which case the sequential assay device will be suitable for quantitative or semi-quantitative assays).

Figure 3:
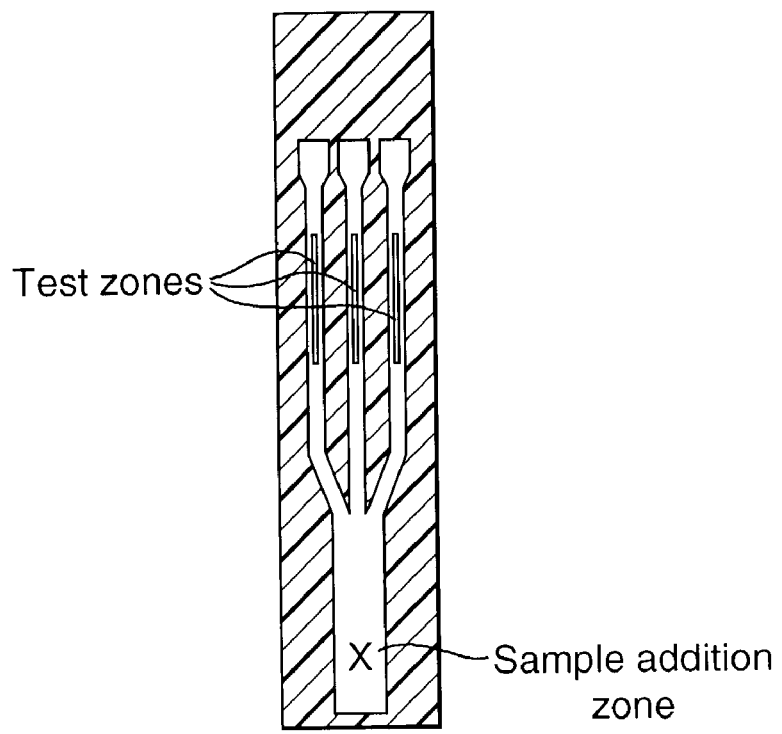

In the assay devices of the invention, the bibulous compartment may comprise a central body having a plurality of channels connected thereto. Such an arrangement is shown in FIGS. 2 and 3. Detection reagents can be provided in each channel. As for the sequential assay device, each such detection reagent may be capable of reacting with a different analyte to produce a detectable effect (in which case the device will be suitable for assaying a liquid sample for a plurality of analytes). Alternatively, each detection reagent may be sensitive to a different concentration of the same analyte (in which case the device will be suitable for quantitative or semi-quantitative assays). Typically, in such assay devices, there are from two to six or more, preferably four, channels connected to the central body.

The test reagents may further comprise a blocking agent such as bovine serum albumin, polyvinyl pyrrolidine, globulin and peptones such as acid- and enzyme-hydrolysed caesin or carboxymethyl cellulose. They may also comprise a carrier buffer such as 10 mM Tris hydrochloride or Tris carbonate. It is particularly preferred that the test reagents comprise such a blocking agent or carrier buffer when the detection reagent reacts with the predetermined analyte in an enzymatic or immunological reaction.

The assay device of the present invention is particularly suitable for conducting immunoassays. In assay devices suitable for conducting immunoassays, the detection reagent is typically a specific binding reagent such as an antigen or an antibody. Typically, the specific binding reagent is an antigen of diagnostic significance, an antibody for an antigen of diagnostic significance, or an antibody which recognises an antibody for an antigen of diagnostic significance.

An antigen of diagnostic significance can be a pathogen. Also, an antigen of diagnostic significance can be an antigen, whose amount in a sample is thought to be related the probability of onset of a disease. Further, an antigen of diagnostic significance may be an antigen whose presence in a sample indicates a clinical condition such as pregnancy.

Examples of antigens of diagnostic significance include human chorionic gonadotrophin, luteinizing hormone, antigens from hepatitis A, B and C viruses, microorganisms responsible for *Chlamydia* or Lyme disease, the HIV virus or pathogens responsible for other sexually transmitted diseases, antigens such as cholesterol which are associated with heart disease, antigens which are indicative of heart attack or other such physiological disorders, antigens associated with Downs Syndrome, antigens associated with feline leukaemia and antigens associated with allergic responses. Typically, when the specific binding reagent is an antibody, it is an antibody for a pathogen such as a virus, a bacterium, or another micro-organism or an antibody which recognises an antibody for a said pathogen.

More preferably, in assay devices suitable for conducting immunoassays, the test reagents comprise:

(a) a labelled analyte or analyte analogue or a labelled said specific binding reagent for an analyte, the labelled specific binding reagent or labelled analyte or analyte analogue being freely mobile when a liquid sample in whose presence the analyte is suspected, is applied to the porous material; and (b) an unlabelled said specific binding reagent for the same analyte, immobilised on the porous material in a detection zone, the relative positioning of the labelled reagent (a) and the detection zone being such that when the liquid sample is applied to the bibulous compartment, the labelled reagent (a) permeates into the detection zone.

The unlabelled reagent (b) is generally immobilised on the porous material by passive adsorption or by means of a said detection anchor compound. An assay device in which the test reagents are provided on the porous material in this way is shown in FIG. 1.

Typically, the reagent (b) is provided within the bibulous compartment and the reagent (a) is provided on a part of the porous material which is not coated with the polymer (b), in such a way as to be chromatographically transported into the bibulous compartment when a liquid sample is applied to the assay device.

Assay devices of the invention in which the test reagents are as defined above can be used to perform both sandwich assays (when the labelled reagent (a) is a specific binding reagent for an analyte) and competition assays (when the labelled reagent (a) is an analyte or analyte analogue). The analyte for which the liquid sample is assayed may be an antigen or an antibody.

Figure 4:
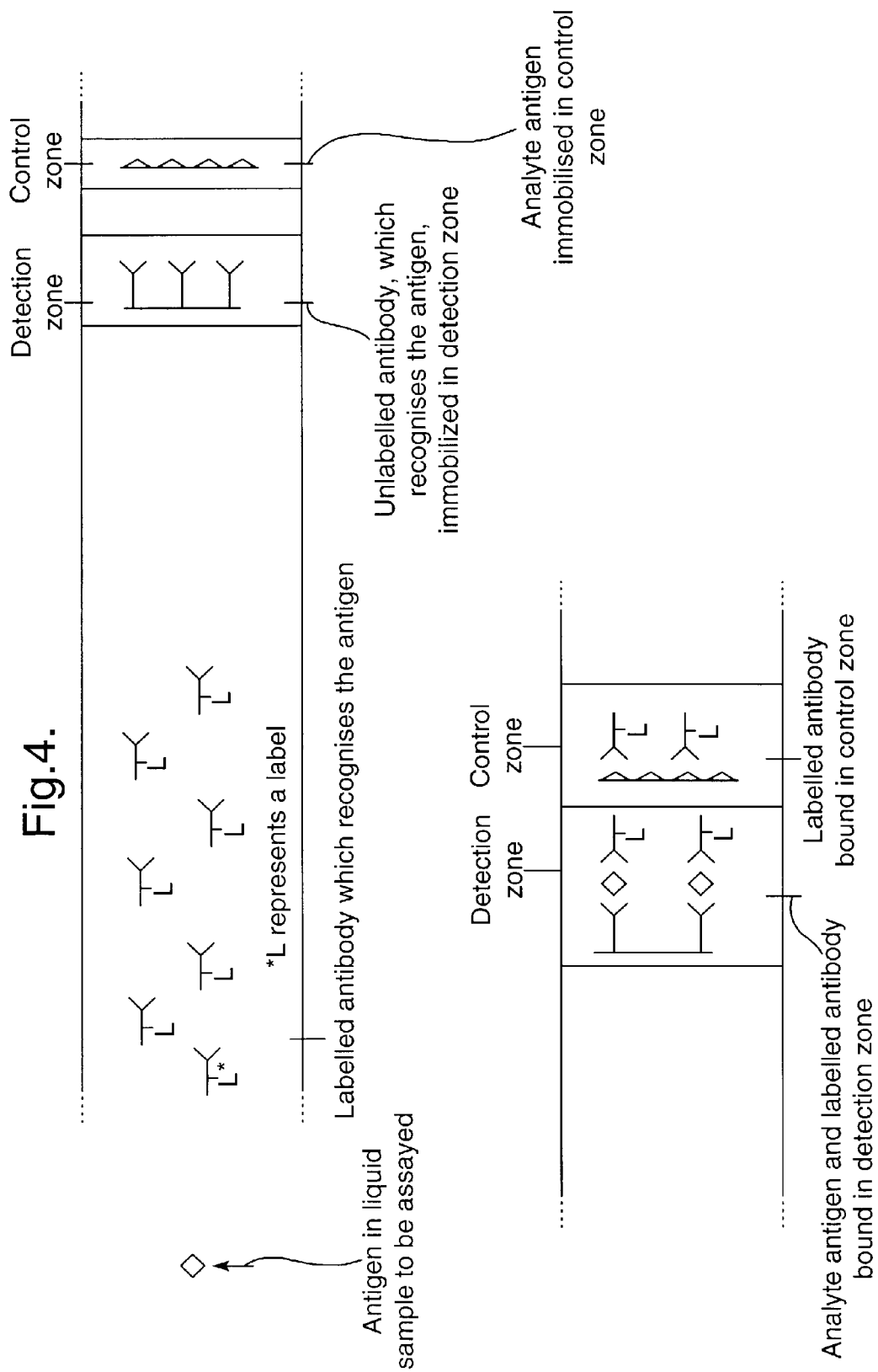
FIG. 4 shows a device for use in a sandwich assay for an antigen.

When the device is intended for use in a sandwich assay, and the analyte for which the liquid sample is assayed is an antigen, the labelled reagent (a) and the unlabelled specific binding reagent (b) are both generally antibodies which recognise the antigen. Clearly, the unlabelled reagent (b) does not bind to the epitope to which the labelled reagent (a) binds, but is specific for a different epitope. An example of such an assay device is shown in FIG. 4.

Figure 5:
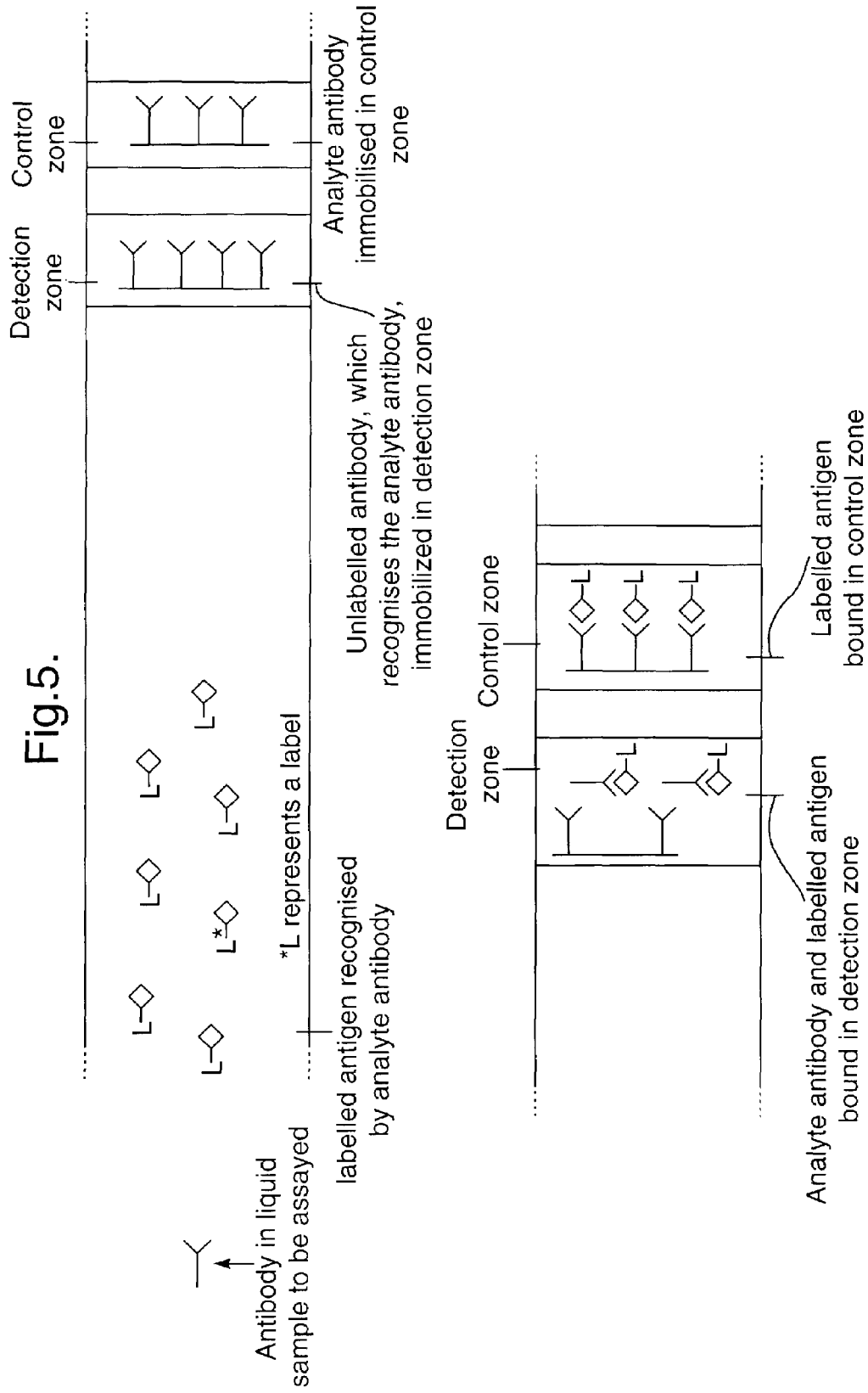
FIGS. 5 and 6 show a device for use in a sandwich assay for antibodies.
Figure 6:
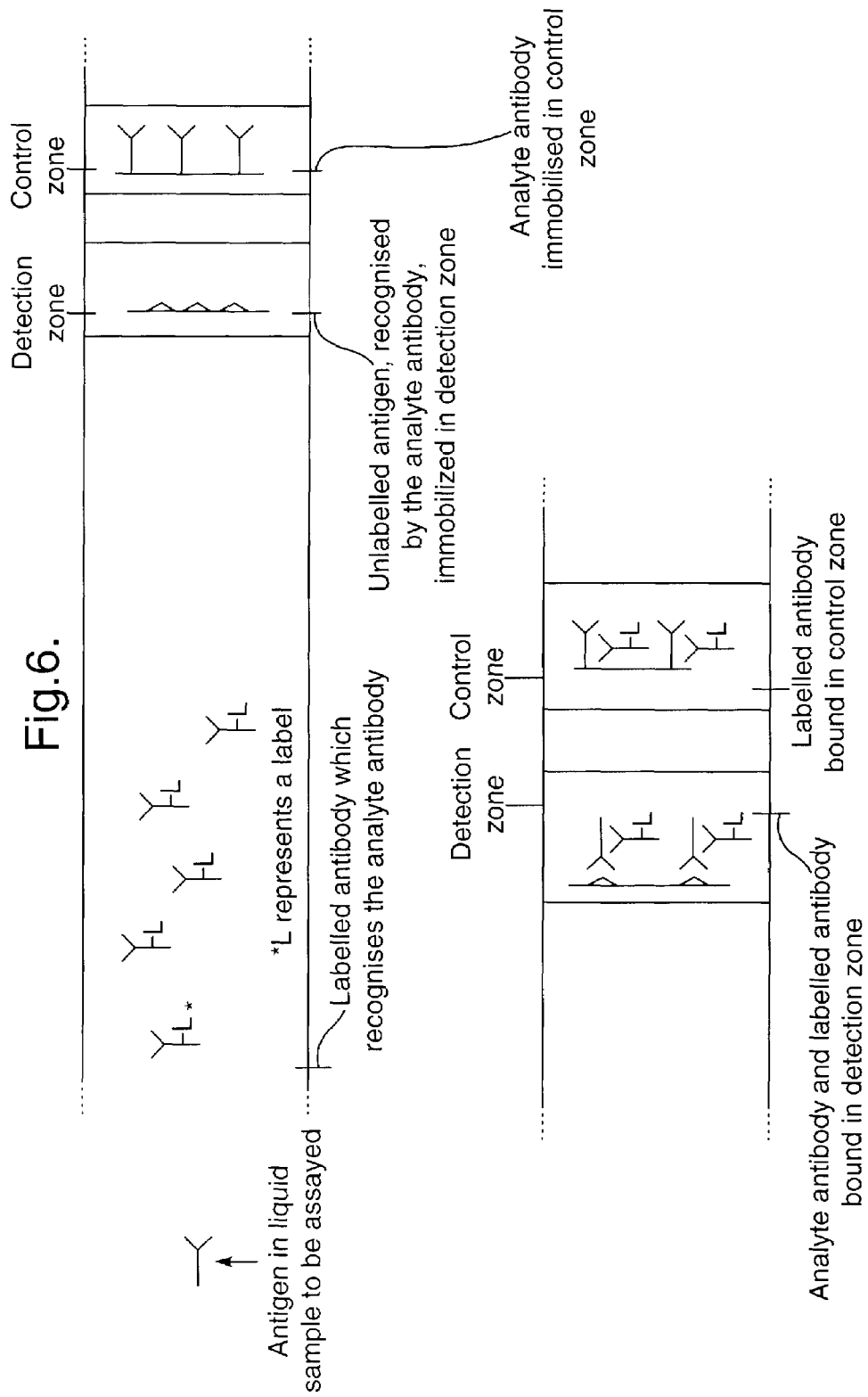

When the analyte for which the liquid sample is assayed is an antibody, the labelled reagent (a) can be an antigen recognised by the analyte antibody, in which case the unlabelled reagent (b) is generally an antibody which recognises the analyte antibody. An example of such an assay device is shown in FIG. 5. Alternatively, the labelled reagent (a) can be an antibody which recognises the analyte antibody, in which case the unlabelled reagent (b) is generally an antigen recognised by the analyte antibody. An example of such an assay device is shown in FIG. 6.

Assay devices in which reagents (a) and (b) are specific binding reagents for an antibody which recognises HIV or feline leukaemia pathogens are particularly preferred.

When the analyte is a human antibody, examples of antibodies which recognise the analyte antibody include antihuman IgG and antihuman IgM.

When the device is intended for use in a competition assay, the unlabelled reagent (b) is generally an antibody when the analyte for which the liquid sample is assayed is an antigen. When the analyte for which the liquid sample is assayed is an antibody, reagent (b) is generally an antigen recognised by the analyte antibody or an antibody which recognises the analyte antibody.

Further test reagents may be present in a control zone, to ensure that the labelled reagent (a) has permeated into the detection zone. These further test reagents typically comprise a specific binding reagent for the labelled reagent (a). When the assay is a sandwich assay, the analyte or an analogue thereof is typically immobilised in the control zone. When the assay is a competition assay, a reagent capable of binding to the label carried by the labelled reagent (a) may be immobilised in the control zone. The positioning of the control zone is generally such that when the liquid sample is applied to the bibulous compartment, the labelled reagent (a) permeates from the detection zone to the control zone.

As used herein, an analogue of an analyte is a compound capable of forming a complex with a specific binding reagent for the analyte.

Preferably, both the labelled reagent (a) and the unlabelled reagent (b) are antibodies, preferably antibodies which recognise a pathogen such as a virus, a bacterium or another micro-organism. In a further preferred embodiment, unlabelled reagent (b) is a said pathogen and labelled reagent (a) is an antibody which recognises an antibody for the said pathogen.

The assay devices of the invention suitable for conducting immunoassays can also be used in a quantitative or semi-quantitative assay or in an assay of a liquid sample for a plurality of predetermined analytes. In devices suitable for use in such assays, the bibulous compartment typically comprises a central body and a plurality of channels connected thereto (FIGS. 2 and 3).

In devices suitable for an immunoassay of a liquid sample for a plurality of predetermined analytes:

a labelled said specific binding reagent for each predetermined analyte or a labelled analyte or analyte analogue corresponding to each predetermined analyte is typically present in the central body, the labelled specific binding reagent or labelled analyte or analyte analogue being freely mobile when a liquid sample in whose presence the analytes are suspected, is applied to the porous material; and each channel connected to the central body typically contains a detection zone in which is immobilised an unlabelled said specific binding reagent for one of the predetermined analytes, the relative positioning of the labelled reagents and the detection zones being such that when the liquid sample is applied to the bibulous compartment, the labelled reagents permeate into each detection zone.

In assay devices suitable for a quantitative or semi-quantitative assay:

a labelled analyte or analyte analogue or a labelled said specific binding reagent for an analyte is typically present in the central body, the labelled specific binding reagent or labelled analyte or analyte analogue being freely mobile when a liquid sample in whose presence the analyte is suspected, is applied to the porous material; and each channel connected to the central body typically contains a detection zone in which is immobilised an unlabelled said specific binding reagent for the analyte, wherein the relative positioning of the labelled reagent and the detection zones is such that when the liquid sample is applied to the bibulous compartment, the labelled reagent permeates into each detection zone, and wherein either (a) each detection zone contains a different concentration of unlabelled specific binding reagent, or (b) one or more, but not all (and preferably all except one), of the channels connected to the central body are calibration channels which contain a zone (i), in which is immobilised a specific binding reagent for the analyte in a quantity sufficient to bind substantially all of the analyte which passes through the zone, and a zone (ii) containing a defined amount of optionally labelled analyte or analyte analogue which is freely mobile when the liquid sample is applied to the porous material, the relative positioning of the zone(s) (i), the zone(s) (ii) and the detection zone(s) in the calibration channel(s) being such that when the liquid sample is applied to the bibulous compartment, liquid sample permeates from the central body first to the zone(s) (i), then to the zone(s) (ii) and then to the detection zone(s).

Typically, the analyte or analyte analogue present in each zone (ii) is labelled when the liquid sample to be assayed contains a high concentration of analyte. Under these circumstances, a large amount of the labelled reagent present in the central body will be bound in each zone (i) (via the analyte), and a sufficient amount of the labelled reagent from the central body may not permeate to the detection zone(s) in the calibration channel(s).

Typically there are from 2 to 6, preferably 4, channels connected to the central body.

Devices suitable for an assay of a liquid sample for a plurality of predetermined analytes or suitable for a quantitative or semi-quantitative assay can be used to perform both sandwich assays and competition assays for antibodies or antigens, as described above. Further test reagents may be present in one or more control zones as described above.

FIGS. 2 and 3 show assay devices of the invention which can be used in an assay of a liquid sample for a plurality of predetermined analytes or in a quantitative or semi-quantitative assay.

Figure 7:
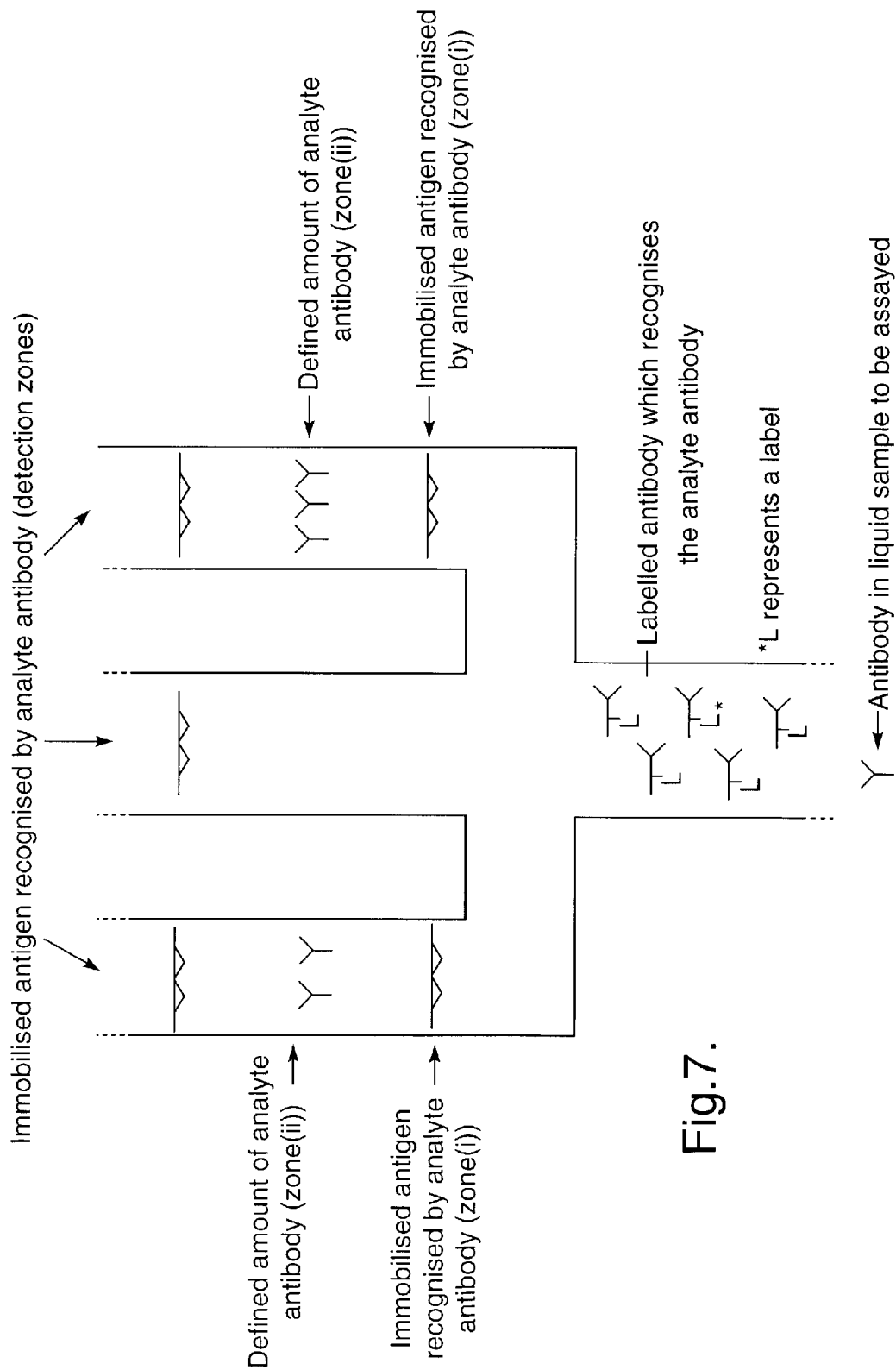
FIG. 7 illustrates a part of the bibulous compartment of an assay device suitable for conducting a semi-quantitative assay for an antibody.

A particularly preferred assay device, suitable for conducting a semi-quantitative assay for an antibody, is shown in FIG. 7. In this device, a labelled antibody which recognises the analyte antibody is present in the central body. All except one of the channels connected to the central body contain a said zone (i), in which is immobilized an antigen recognised by the analyte antibody, and a said zone (ii), each zone (ii) containing a different predetermined amount of the analyte antibody. Each channel connected to the central body also contains a detection zone in which is immobilised an antigen which is recognised by the analyte antibody.

Comparison of the signals generated in the detection zones after completion of the assay, gives an indication of the concentration of analyte antibody in the liquid sample.

The labelled test reagents can be labelled by any conventional label. Preferably, the label is an enzyme label, a radioactive label, a fluorescent label, dyed latex microspheres, a gold label or a functionalized polysaccharide label. More preferably, the label is capable of generating a visual signal. The label may be attached by conventional means.

For certain assays, it may be advantageous to specifically direct or control the rate of the flow of the liquid sample over the detection zone(s), thereby encouraging greater contact between the analyte in the liquid and the reagents immobilised in the detection zone(s) in order to effect an intensification of the signal generated by the label. The shape of the bibulous compartment may be adapted to achieve this. For example, the bibulous compartment can be narrower at the detection zone(s) than in the region of the porous material where the liquid sample is added. Such an arrangement is shown in FIG. 1.

The shape of the bibulous compartment may also be such as to create a trapping zone at which labelled reagent will concentrate. Such a trapping zone can be used to indicate that successful chromatography has taken place. It can therefore act as an independent control by providing a "ready to read" indicator. A trapping zone can consist, for example, of a partial barrier across the bibulous compartment. Such a barrier can be formed by the doping polymer, as is shown in FIG. 1.

The assay device of the invention may further comprise a filter to remove unwanted particulate matter from the liquid sample to be assayed. Generally, the filter is provided across the entrance to the bibulous compartment so that the liquid sample can be applied to the assay device through the filter.

For example, the filter may comprise a polymer having defined pore sizes provided across the entrance to the bibulous compartment. Such an integral Filter can act as a semi-permeable barrier to remove unwanted particulate material such as detritus from water samples. Alternatively, the filter may comprise a said porous material provided across the entrance to the bibulous compartment, a part of which being optionally coated with the coating polymer (b). Such a filter could remove matter such as red blood cells from the liquid sample to be assayed. The said doping polymer may be incorporated into a part of such a filter so as to define a channel in the filter. Such a channel may be useful for directing the liquid sample to the entrance of the bibulous compartment.

Preferably, the assay device of the invention is a substantially planar strip such as a dipstick, which chromatographically transports the liquid sample along the strip (a "lateral flow device"). However, the assay device may also chromatographically transport the liquid sample through the thickness of the porous material (a "tangential flow device").

In a tangential flow device, a said doping polymer is incorporated into a part of the porous material as described above, the channel defined by the doping polymer running through the body of the porous material. The channel is thus enclosed by the porous material on all sides. The coating polymer (b) is not essential in a tangential flow device.

The present invention therefore also provides an assay device comprising:
(a) a substrate comprising:
 (i) a porous material capable of chromatographically transporting a liquid; and
 (ii) one or more test reagents for an assay provided on the porous material; and
(b) a doping polymer impermeable to the liquid which the porous material is capable of transporting, incorporated into a part of the porous material so as to define a channel running through the body of the porous material, the or each test reagent being provided on the porous material in the channel defined therein.

Preferred doping polymers are as defined above.

Such a tangential flow device may comprise, over the entrance to the channel in the porous material, a polymer having defined pore sizes. Such a polymer can act as a semi-permeable membrane as explained above. Further, such a tangential flow device may comprise, across the exit from the channel in the porous material, a layer or coating impermeable to the liquid which the porous material is capable of transporting. The impermeable layer or coating may, for example, comprise a said coating polymer (b) or a silane layer bonded to the porous material.

Many such tangential flow devices can be provided on a single sheet of porous material such as a single sheet of paper. The tangential flow devices thus provided can be used to conduct assays in a similar way to a conventional microtitration plate.

Also provided is a method of assaying a liquid sample for the presence or absence of a predetermined analyte, which method comprises:
(a) contacting the liquid sample with the bibulous compartment of a device according to the invention;
(b) allowing the porous material to transport chromatographically the liquid sample; and
(c) determining the presence of the predetermined analyte in the liquid sample.

The present invention also provides the use of an assay device of the invention to assay a liquid sample for a predetermined analyte. Also provided is a test-kit containing an assay device of the invention.

Further, the present invention provides a process for preparing an assay device of the invention, which process comprises:
(a) providing a porous material capable of chromatographically transporting a liquid;
(b) providing one or more test reagents for an assay on the porous material; and
(c) attaching a transparent, water-impermeable coating polymer to the thus-obtained material by contacting the material with a solution or suspension of the coating polymer.

In step (c) the porous material is coated with the transparent, water-impermeable coating polymer. Where the coating polymer is a biological polymer such as a heteropolysaccharide, the material is typically first contacted with a gel accelerating agent and then contacted with the solution or suspension of the coating polymer.

In some cases the coating polymer may be applied in step (c) by contacting the material with the coating polymer in liquid form.

The coating polymer may be applied by roller coating methods known to those of skill in the art, particularly when it is a synthetic polymer.

Preferably, the process of the invention comprises the additional step, between steps (a) and (b), of applying a doping polymer impermeable to the liquid which the porous material is capable of transporting, to part of the porous material, so as to define a channel in the porous material, the or each test reagent being provided on the porous support in step (b) in the channel defined therein.

The doping polymer may be applied by means of a computer-controlled air brush or, preferably, by applying the doping polymer to the porous material after attaching a template to both sides of the porous material. This can be done, for example, by standard screen printing techniques.

The gel-accelerating agent is a compound capable of promoting cross-linking of the coating polymer. It may also be described as a cross-linking agent. A gel-accelerating agent is not required when the polymer is a synthetic polymer such as an acrylate polymer. Suitable gel-accelerating agents include inorganic salts such as calcium chloride, nitrogen-containing polymers such as polyethyleneimine, organic ammonium salts such as hexadecylammonium bromide, proteins such as cellulases and cationic resins such as neutral curing poly(aminoamide) chemicals (for example Kymene® SLX).

Preferably, the process of the invention further comprises:
(d) contacting the thus obtained device with one or more compound(s) selected from acrylic polymers, gelling polysaccharides and polyvinyl alcohols to form a further layer, which is preferably a transparent glossy layer, on the device.

Preferably the further layer is obtained by dipping the assay device into a solution selected from solutions comprising from 0.5% to 1.5% w/v alginic acid, solutions comprising from 7.5% to 12.5% w/v polyvinyl alcohol, solutions comprising 100% w/v Primal B-60A, solutions comprising from 25% to 100% w/v Acrysol WS-24, and solutions comprising from 40 to 60% w/v, preferably about 47% w/v, Primal B-60A which have a Primal B-60A: polymethacrylic acid ratio of from 90:10 to 70:30 or a Primal B-60A:Primal B85 ratio of from 95:5 to 90:10. Typically, all of the above solutions are aqueous solutions.

Typically, when the water-impermeable coating polymer is a said biological polymer, the process of the invention further comprises a washing step before step (a), in which the porous material is contacted with an aqueous solution of mono, di or tri-valent metal ions, such as potassium, calcium or aluminium ions. The washing step is generally effected by passing the porous material through a dip tank containing the solution of metal ions, and then drying the porous material in an air box.

A said tangential flow assay device may be prepared by providing one or more said test reagents on a said porous material and applying a said doping polymer thereto as described above.

In its broadest aspect the invention provides the use of a polymer impermeable to a liquid, for controlling the flow of the liquid though a porous material which is capable of chromatographically transporting the liquid.

The following Examples illustrate the invention.

EXAMPLES 1-5

80 mm lengths of unmodified chromatography paper (Whatman 31ET or 3MM) composed of pure cellulose fibers with a mean matrix pore size of 4-6 µm were passed through a dip tank containing an aqueous solution of 200 mM calcium chloride. They were then dried in an air tank and cut to a final dimension of 8×80 mm.

Pores in part of the strips thereby obtained were blocked by the incorporation of the acrylic polymer Primal B-60A applied at room temperature (RT). A channel in the strip was formed by clamping polycarbonate templates either side of the paper and applying the polymer. The polymer was left to dry at room temperature for approximately 2 hours.

Type I carrageenan (1.5% wv$^{-1}$) in distilled water was then heated to 80° C. until completely in suspension. Once in suspension the polymer was cooled to, and maintained at, 45° C.

The polymer was applied to the paper in such a way as to achieve surface polymerisation with minimum gel permeation of the cellulose matrix. To achieve this a variety of gel-accelerating agents were used as set out in Table 1.

Test strips were initially dipped into an aqueous solution of the gel-accelerating agent followed by an immediate dip into the warm carrageenan suspension. This process was repeated three times to build a continuous surface coat, finishing with a final dip in the gel-accelerating solution. Coated strips were left to dry overnight at either room temperature or 37° C.

A further coating layer was subsequently applied to the coated papers thereby obtained using a variety of polymer and co-polymer mixtures as set out in Table 1.

The coated papers were dipped twice into the further coating polymer and left to dry at room temperature for 2 hours.

TABLE 1

| Example | Gel-Accelerating Agent | Further Coating Polymer |
|---|---|---|
| 1 | 200 mM Calcium chloride | Mixture of Primal B-60A (100% w/v) and Orotan 165* (21% w/v) |
| 2 | polyethyleneimine (2% w/v) | as above |
| 3 | Celluclast (5.0% w/v) | as above |
| 4 | Kymene SLX (1.0% w/v) | as above |
| 5 | hexadecyltrimethyl ammonium bromide | as above |

*Orotan 165 is an ammonium salt of polymethacrylic acid.

EXAMPLES 6 TO 10

The process of Examples 1 to 5 was repeated, except that Type II carrageenan was used as the doping polymer in place of Primal B-60A.

Type II carrageenan (1% w/v) in distilled water was heated to 90° C. with constant stirring until all the polymer was in suspension. Once in suspension the polymer was maintained at 70° C., and applied to both sides of the paper, to which a polycarbonate template had been attached. The paper was then left to dry for approximately 2 hours at room temperature.

The strips were coated with Type I carrageenan and a further coating layer as set out in Examples 1 to 5. The gel-accelerating solutions and further coating polymers used are set out in Table 2.

TABLE 2

| Example | Gel-Accelerating Agent | Further Coating Polymer |
|---|---|---|
| 6 | 200 mM Calcium chloride | Mixture of Primal B-60A (100% w/v) and/or Orotan 165* (21% w/v) |
| 7 | polyethyleneimine (2% w/v) | as above |
| 8 | Celluclast (5.0% w/v) | as above |
| 9 | Kymene SLX (1.0% w/v) | as above |
| 10 | hexadecyltrimethyl ammonium bromide | as above |

Orotan 165 is an ammonium salt of polymethacrylic acid

EXAMPLE 11

Generation of an Immuno-Diagnostic Lateral Flow Device

Application of Doping Polymer

Polyvin Gloss was applied to sheets of unmodified chromatography paper (200×280 mm) (Whatman 31ET, 3MM or Schleicher & Schuell 22/2, 3324, 2668) using conventional screen printing techniques. The polymer was applied as a screen printed template to both sides of the paper. The printing defined individual lateral flow formats each having a channel of undoped paper. The dimensions of the lateral flow formats were 15×85 mm. After application of the doping polymer, the sheets were cut into the individual lateral flow formats.

Application of Test Reagents

Using a Gilson pipette, 5 µl of blocking buffer was applied to the lateral flow format in a continuous stripe across the width of the channel 15 mm from the bottom end of the strip. This stripe was defined as the "origin".

The strip was then dried in an oven (60° C.) for 5 mins then left at room temperature for 30 mins.

Gold labelled antibodies specific for human chorionic gonadotrophin were applied as a continuous stripe across the width of the channel at the origin.

Unlabelled antibody specific for the gold labelled antibody was then applied as a continuous stripe across the width of the channel 28 mm from the bottom end of the strip. This was defined as the "detection zone". The strip was then allowed to air dry at room temperature for at least one hour.

Application of Primary and Secondary Coating Polymers

The individual lateral flow strips onto which the test reagents had been applied were dipped into a warm (38 ±1° C.) solution of coating polymer (b) (1.5% wv$^{-1}$ agarose) twice, up to a depth of 65 mm from the top of the strip, leaving the origin uncoated. They were then dried overnight at room temperature.

The primary coated strips were dipped twice into a mixture 90:10 Primal B-60A; Orotan 165 (the polymer (c) up to a depth of 65 mm from the top of the strip, leaving the origin uncoated. They were then allowed to air dry overnight at room temperature.

Running of Test Strips

The tests were developed by running the strips in a sample of synthetic urine buffer into which human chorionic gonadotrophin at various concentrations was added. A distinct pink stipe at the detection zone showed that the strip had successfully developed and that the analyte (human chorionic gonadotrophin) had been detected.

EXAMPLE 12

The process of Example 11 was repeated except that, following the application of the test reagents, a coating polymer of Primal B60 was applied using a K hand Coater (RK Print-Coat Instruments Ltd). The strips were then air dried at room temperature for 30 mins.

Barriercoat DC1708, a modified styrene acrylate polymer emulsion (Dussek Campbell) was roller coated onto the coated strips in a similar fashion, up to a depth of 65 mm from the top of the strip, leaving the origin uncoated. The strips were then air dried at room temperature for 30 mins.

EXAMPLE 13

Tangential Flow Assay Device for the Enzymatic Detection of Glucose

The following procedure describes the production of a tangential flow assay device for the detection of glucose.

The principle behind the detection of glucose by this reaction is as follows:

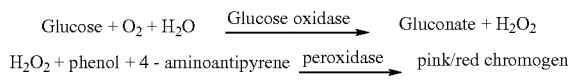

The glucose assay reagents were prepared as follows:

1. Preparation of Phenol Reagent 1.2±0.1 g phenol were weighed into a 100 ml screw-capped bottle and 100±1 ml of 0.1 M phosphate buffer pH 7.0 was added. The mixture was stirred well until completely dissolved. The bottle was wrapped in aluminium foil to exclude light from the solution.

2. Preparation of 4-aminoantipyrene Reagent 0.4±0.1 g of 4-aminoantipyrene were weighed into a 100 ml screw-capped bottle and 100±1 ml of 0.1 M phosphate buffer pH 7.0 were added. The mixture was stirred well until completely dissolved. The bottle was wrapped in aluminium foil to exclude light from the solution.

3. Preparation of Peroxidase Reagent

A sample of peroxidase solution containing 800 IU/ml was prepared by taking a sample of peroxidase with an activity of X IU/mg, weighing 800/X±0.1 mg into a 1.5 ml Eppendorf tube and adding 1.0±0.1 ml 0.1 M phosphate buffer, pH 7.0. This reagent must be prepared freshly each time.

4. Preparation of Glucose Oxidase Reagent

A glucose oxidase solution containing 250 IU/ml was prepared by taking a sample of glucose oxidase with an activity of X IU/mg and Y mg/ml, pipetting 250/XY±0.01 ml into a 1.5 ml Eppendorf tube and adding 1±0.1 ml 0.1 M phosphate buffer, pH 7.0. This reagent must be prepared freshly each time.

5. Preparation of the Glucose Assay Reagent

20±1 mg of carboxy methyl cellulose (CMC) was weighed into a 1.5 ml Eppendorf tube and the following reagents were added:

200±1 µl Phenol reagent
200±1 µl 4-aminoantipyrene
200±1 µl Peroxidase reagent
200±1 µl Glucose oxidase reagent
200±1 µl 0.1 M phosphate buffer, pH 7.0

The reagents were mixed well and kept on ice until required.

Application of Doping Polymer

Sheets of unmodified chromatography paper (200×280 mm; Whatmans 31ET, 3MM or SS papers) were screen printed with Polyvin Gloss, using conventional screen printing techniques, applied as a screen printed template defining tangential flow formats to both sides of the paper. The printing defines individual tangential flow test wells.

The printed sheet was similar in format to a microtitration plate.

After application of the doping polymer, the sheets were cut into individual tangential flow formats with 5 wells per strip (10×85 mm). Each well could hold around 5 µl of liquid sample.

Application of Test Reagents

Glucose assay reagent (10±1 µl) as defined above was added to each of the wells printed onto the test strip and allowed to air dry at room temperature for 30 mins.

The strips were stored in aluminium foil to exclude the light at room temperature.

Preparation of a Calibration Standard Strip

A calibration standard strip was prepared at the same time as the sample strips so that a real time comparison could be made when the sample strips were developed.

The glucose calibration standards (10±1 µl) were prepared by weighing 1.802±0.002 g D-glucose into a 100 ml volumetric flask and adding 80 ml distilled water with stirring until the glucose had dissolved completely. The solution was then made up to 100 ml with distilled water. This provided a stock solution of 100 mM, D-glucose, which was used to make 2-10 mM standards by serial dilution. Standards were stored at −20° C. until used.

10 µl±1 µl of calibration standard was then loaded into the reagent-loaded wells. After 1 minute at room temperature, coloration developed within the wells (pink to red). The colour intensity is related to the concentration of glucose in the standard.

The colour scale produced using the calibration strip was used to compare the colour produced by the sample, to give an indication of the concentration of glucose in the sample.

Application of Sample to Test Strip

10±1 µl of sample was loaded into each of the reagent-loaded wells. After 1 min at room temperature, coloration developed within the wells (pink to red).

The colour development of this strip was compared with the calibration standard strip as described to give an indication of the glucose concentration of each sample.

EXAMPLE 14

Tangential Flow Assay Device for the Detection of Nitrite

The process of Example 12 was repeated, except that nitrite assay reagents were used in place of glucose assay reagents. The nitrite assay reagents were prepared as follows:

1. Sulphanilamide Reagent

40±0.5 mg sulphanilamide and 2.0±0.1 mg N-1-naphthylethylenediamine dihydrochloride were weighed into a 1.5 ml Eppendorf tube. 1±0.1 ml of o-phosphoric acid (10% vv$^{-1}$) was added and the mixture was stirred until dissolved.

2. Preparation of Nitrite Calibration Standards 48.2±0.1 mg of nitrite was weighed into a 500 ml beaker and 400 ml deionised water was added. The mixture was stirred until dissolved. The contents of the beaker was then transferred with washings using deionised water into a 1 L volumetric flask. The solution was made up to 1 L with deionised water and mixed well. A 10 mgl$^{-1}$ (10 ppm) nitrite (NO$^{2-}$) stock solution was thereby obtained which was used to prepare standard solutions from 1 to 8 ppm nitrite. The standards were stored at −20° C. until used.

EXAMPLE 15

Lateral Flow Assay Device for the Detection of Nitrite

Using Whatman 31ET paper as porous material in such a lateral flow assay device led to chromatographic transport of the chromophore used in the nitrite test during the course of the test. This had the effect of separating the colour on the paper rather than producing a definitive colour change in the test region of the device. A charged porous material was therefore used to anchor the colour molecule.

Thus, Whatman ion exchange paper P81, containing the modified ion exchange cellulose, cellulose phosphate, was used as the porous support in place of 31 ET and the masking polymer was applied as in Example 11. Nitrite test reagents prepared as in Example 14 were applied to a detection zone region of the device. The nitrite test chromophore, a positively charged species, was anchored in place by the negative charge of the cellulose phosphate. Thereafter when the test was run the other reagents moved with the sample containing the nitrite and reacted with the anchored chromophore resulting in a sharp band of colour which could be related to the nitrite concentration in the sample.

The invention claimed is:

1. An assay device comprising:
   (a) a substrate comprising (i) a porous material capable of chromatographically transporting a liquid and (ii) one or more test reagents for an assay provided on the porous material; and
   (b) a doping polymer impermeable to the liquid which the porous material is capable of transporting, incorporated into a part of the porous material so as to define a channel in the porous material, the one or more test reagents being provided on the porous material in the channel defined therein.

2. The assay device according to claim 1 comprising (i) a polymer having defined pore sizes over the entrance to the channel in the porous material and/or (ii) a layer or coating impermeable to the liquid which the porous material is capable of transporting across the exit from the channel in the porous material.

3. A method of assaying a liquid sample for the presence or absence of a predetermined analyte, which method comprises:
   (a) contacting the liquid sample with the bibulous compartment of a device according to claim 1;
   (b) allowing the porous material to transport chromatographically the liquid sample; and
   (c) determining the presence of the predetermined analyte in the liquid sample.

4. A test-kit containing a device according to claim 1.

5. A process for preparing an assay device which process comprises:
   (a) providing a porous material capable of chromatographically transporting a liquid;
   (b) providing one or more test reagents for an assay on the porous material; and
   (c) applying a doping polymer impermeable to the liquid which the porous material is capable of transporting, to part of the porous material, so as to define a channel in the porous material, the one or more test reagents being provided on the porous support in step (b) in the channel defined therein.

6. The process according to claim 5 wherein the doping polymer defines a plurality of tangential flow test wells.

7. The process according to claim 5 wherein the doping polymer is applied by screen printing.

8. The process according to claim 7 wherein the doping polymer is applied to a sheet of porous material by screen printing each major surface of said sheet.

9. The process according to claim 5 wherein the doping polymer is an acrylic polymer, a vinyl acrylic polymer or a hetropolysaccharide.

10. The process according to claim 5 further comprising:
    (d) attaching a water-impermeable coating polymer to the thus obtained material by contacting the material with a solution or suspension of the coating polymer.

11. The process according to claim 10 further comprising:
    (e) contacting the thus obtained device with one or more compounds selected from the group consisting of acrylic polymers, gelling polysaccharides and polyvinyl alcohols to form a transparent glossy layer on the device.

* * * * *